United States Patent [19]

Karthaus et al.

[11] Patent Number: 5,283,035
[45] Date of Patent: Feb. 1, 1994

[54] METHOD FOR RECOVERING A STERILIZING GAS

[75] Inventors: Michael Karthaus, Neuss; Peter Hermanns, Wesel; Klaus Hermanns, Hünxe, all of Fed. Rep. of Germany

[73] Assignees: Herco-Kuhltechnik Hermanns U. Co. GmbH, Wesel; Air Products GmbH, Hattingen, both of Fed. Rep. of Germany

[21] Appl. No.: 963,821

[22] Filed: Oct. 20, 1992

[30] Foreign Application Priority Data

Nov. 21, 1991 [DE] Fed. Rep. of Germany ....... 4138321

[51] Int. Cl.⁵ .................. A61L 2/16; A61L 9/00; F25J 3/00
[52] U.S. Cl. ............................ 422/31; 62/11; 422/3; 422/28; 422/34
[58] Field of Search .............. 422/31, 30, 34, 28, 422/3, 291, 32, 33; 62/11; 55/33, 80

[56] References Cited

U.S. PATENT DOCUMENTS

| | | | |
|---|---|---|---|
| 3,549,312 | 12/1970 | Ernst | 422/31 |
| 3,989,461 | 11/1976 | Skoycypec et al. | 422/31 |
| 4,130,393 | 12/1978 | Fox | 422/31 |
| 4,150,494 | 4/1979 | Rothchild | 34/28 |
| 4,249,917 | 2/1981 | Tarancon | 55/48 |
| 4,812,292 | 3/1989 | Joslyn | 422/31 |
| 4,822,563 | 4/1989 | Joslyn | 422/31 |
| 4,954,315 | 9/1990 | Brahmbhatt | 422/31 |
| 5,128,101 | 7/1992 | Boynton | 422/31 |

FOREIGN PATENT DOCUMENTS

| | | |
|---|---|---|
| 0130319 | 5/1984 | European Pat. Off. |
| 0125520 | 11/1984 | European Pat. Off. |
| 0326985 | 1/1989 | European Pat. Off. |
| 0417592 | 9/1990 | European Pat. Off. |
| 2745961 | 4/1979 | Fed. Rep. of Germany |
| 4040839 | 12/1990 | Fed. Rep. of Germany |
| 4117306 | 5/1991 | Fed. Rep. of Germany |

OTHER PUBLICATIONS

EPO Search Report List for EP A 92117278.9.

*Primary Examiner*—Robert J. Warden
*Assistant Examiner*—L. M. Crawford
*Attorney, Agent, or Firm*—Ratner & Prestia

[57] ABSTRACT

In a method and an apparatus for recovering a sterilizing gas, in particular ethylene oxide (ETO), materials to be sterilized are sterilized in a sterilizing chamber with a sterilizing gas and a gas flow is withdrawn from the sterilizing chamber. At least part of the sterilizing gas contained in said gas flow is liquefied and separated. The gas flow freed from liquefied sterilizing gas is returned to the sterilizing chamber whilst at the same time at least a part of the separated sterilizing gas is replaced by addition of inert-rendering gas, reducing the concentration of the sterilizing gas in the sterilizing chamber.

13 Claims, 1 Drawing Sheet

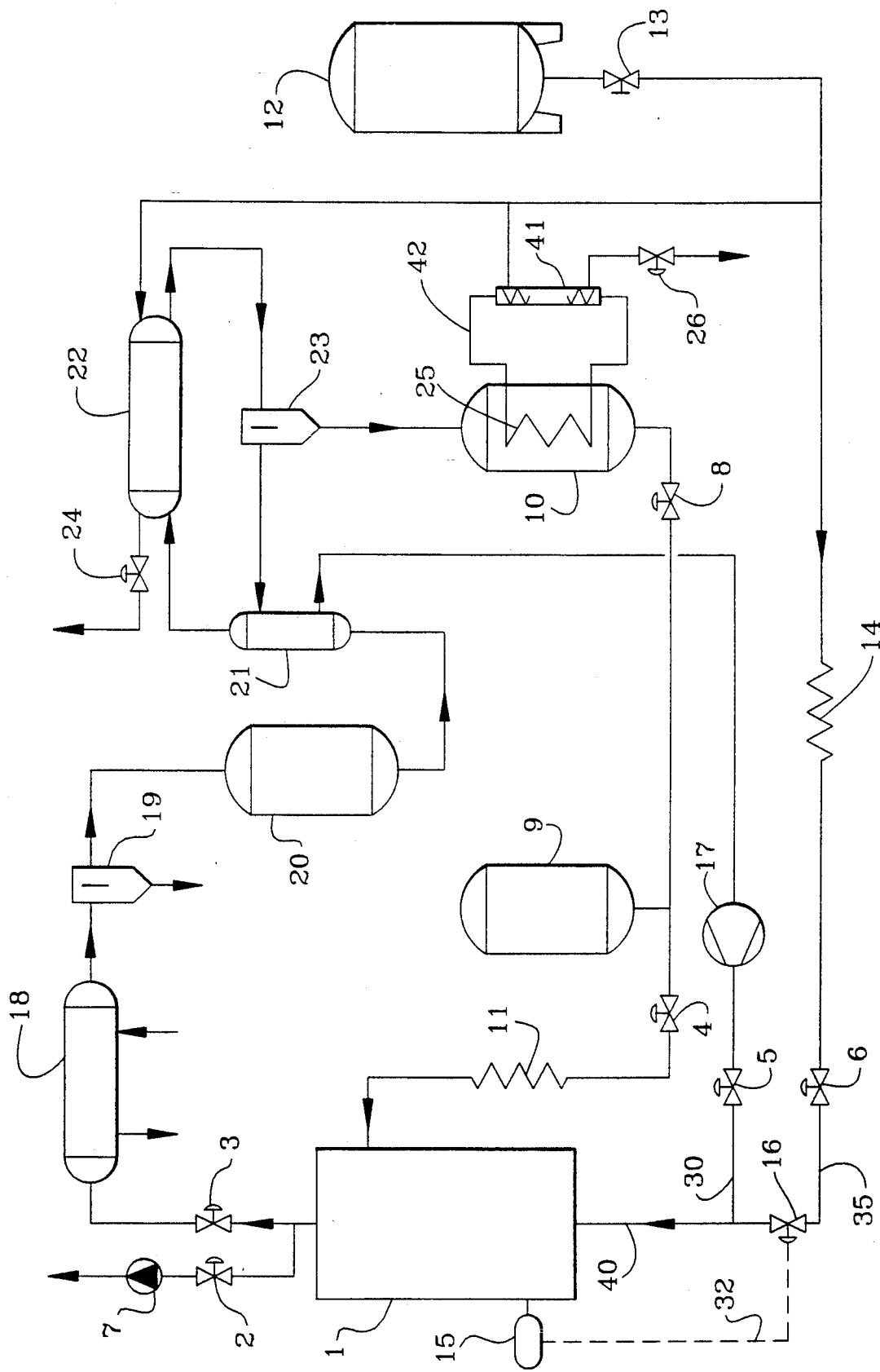

METHOD FOR RECOVERING A STERILIZING GAS

BACKGROUND OF THE INVENTION

1. Field of the Invention

The invention relates to a method and apparatus for recovering a sterilizing gas, in particular ethylene oxide, in which materials to be sterilized are sterilized in a sterilizing chamber with a sterilizing gas. A gas flow is withdrawn from the sterilizing chamber and at least a part of the sterilizing gas contained therein is separated from the gas flow.

2. Description of the Prior Art

Usually, alkylene oxides, in particular ethylene oxide, are used as sterilizing gases which are generally mixed with gases which render them inert, such as Freon (dichlorodifluoromethane) or inert gases, in particular nitrogen. For costs and environmental reasons the sterilizing gas mixtures, i.e. the actual sterilizing gas and the other constituents rendering them inert, are not simply released into the environment after a sterilizing operation but are recovered and used again.

Thus, US-PS 3,549,312 discloses a method and an apparatus for recovering alkylene oxide and the admixed inert constituents in which the mixture of alkylene oxide and the inert additives extracted from a sterilizing chamber are supplied to a precooler and subsequently to an absorber. The mixture freed from moisture in the absorber then passes to a condenser for liquefaction of the alkylene oxide and the admixed Freon R 12 and thereafter to a reservoir for intermediate storage of the liquid mixture. This mixture can finally be supplied to the sterilizing chamber again from the reservoir subjected to excess pressure. A disadvantage with this recovery method is that the sterilizing chamber is pumped out after a sterilizing cycle in order to supply the gas or gas mixture to the connected recovery section of the apparatus and to be able to use it in the following sterilizing cycle. In a recovery method according to U.S. Pat. No. 3,549,312 during the pumping of the sterilizing gas or the gas mixture, simultaneously ambient air is allowed into the sterilizing chamber. Although the admitted air and the sterilizing gas or gas mixture to be pumped off have large density differences and thus remain separate from each other in a natural manner, there is a possibility, that in particular towards the end of the pumping operation to an increasing extent in and undesirable manner ambient air gets into the recovery apparatus. This danger is present precisely because the sterilizing chamber must be pumped down to small sterilizing gas residues in order to be able to open said chamber thereafter for the next sterilizing cycle.

According to a method disclosed in EP-A 0 130 319 for purifying ethylene oxide or a mixture of ethylene oxide and a fluorinated hydrocarbon, the sterilizing chamber subjected to excess pressure during the sterilizing is first relieved of pressure after each sterilizing process and thereafter evacuated with an oil-free operating vacuum pump down to a pressure of between 10 and 100 mbar. The discharged and thereafter extracted gases are purified and recovered in order to be made available for a new sterilizing operation. This remaining evacuation down to at least 100 mbar is intended to keep the loss of sterilizing gas down to an acceptable level. In an apparatus operating by this method, within the recovery section of the sterilizing apparatus, complicated pump and cooling systems are necessary for evacuating the sterilizing chamber. Furthermore, during the recovery itself, the pressure in the components and conduit systems of the recovery section changes continuously from the initial pressure in the chamber, lying above atmospheric pressure, down to the pressure of 10 to 100 mbar.

A method and an apparatus for recovery of a sterilizing gas, according to which after a sterilizing process the sterilizing gas is likewise pumped out of the sterilizing chamber and recovered in a recovery cycle is disclosed in German patent application no. 41 17 306.6, which was not previously published.

A further method and an apparatus for recovery of at least one component of a sterilizing gas is disclosed in EP-A-0 326 985. To discharge the gas mixture from the sterilizing chamber, it is proposed in the case of a chamber pressure lying close to atmospheric pressure to force a gas, for example nitrogen, at a higher pressure into the sterilizing chamber and thereby expel the sterilizing gas. The chamber pressure here will lie at least at times above the atmospheric pressure, thereby increasing the danger of leakage losses, i.e. escape of toxic sterilizing gas to the environment. Another disadvantage is the high nitrogen consumption on expelling the sterilizing gas.

Furthermore, it is known from EP-A-0 417 592, in the recovery of solvents collecting in continuously conducted production processes, for example on drying coated video and audio tapes, to fill the dryer with an inert gas and to recover the solvent vapours arising during drying together with said inert gas in a solvent recovery cycle and to return the gas freed from solvent vapours to the dryer again. In a removable apparatus for such a solvent recovery plant as apparent from German patent application P 40 40 389, which was not previously published, mixture can be withdrawn and simultaneously pure inert gas supplied to the dryer not only via the solvent cycle but also via an additional exit and inlet conduit. The objective of this is to enable the gas atmosphere of the dryer to be brought within a very short time to normal values again or maintained within the admissible values in the event of trouble in the dryer.

SUMMARY OF THE INVENTION

The object of the present invention is to avoid the disadvantages which occur in the methods and apparatuses known in the prior art for recovery of a sterilizing gas. In particular, complicated evacuating systems within the recovery apparatus are to be dispensed with, the operational reliability on removing the sterilizing gas from the sterilizing chamber and recovery thereof increased and the amount of inert gas necessary for the sterilizing gas recovery reduced.

The invention therefore proposes in a method for recovering a sterilizing gas, in particular ethylene oxide (ETO), in which the materials to be sterilized are sterilized in a sterilizing chamber with a sterilizing gas, and a gas flow is extracted from the sterilizing chamber and is freed from at least a part of its sterilizing gas by liquefaction thereof and separation of the liquefied sterilizing gas in a separator, the improvement in which the gas flow freed from the liquefied sterilizing gas is returned to the sterilizing chamber and at the same time at least a part of the liquefied sterilizing gas is replaced by addition of inert-rendering gas, reducing the concentration of the sterilizing gas in the sterilizing chamber.

Further advantageous and expedient developments of the invention, which are not self-evident, are set forth in the subsidiary claims. In a method and an apparatus for recovering a sterilizing gas, in particular ethylene oxide (ETO), materials to be sterilized are sterilized in a sterilizing chamber with a sterilizing gas and a gas flow is withdrawn from the sterilizing chamber. At least a part of the sterilizing gas contained in said gas flow is separated. According to the invention, the gas flow freed from the separated sterilizing gas is returned to the sterilizing chamber whilst at the same time at least a part of the separated sterilizing gas is replaced by addition of inert-rendering gas to reduce the concentration of the sterilizing gas in the sterilizing chamber.

In that on the one hand, sterilizing gas, i.e. pure sterilizing gas or a gas mixture containing sterilizing gas, is withdrawn from the sterilizing chamber and on the other hand the gas flow freed from separated sterilizing gas is returned to the sterilizing chamber, a continuous sterilizing gas recovery can be obtained with continuously diminishing amounts of separated sterilizing gas and continuous neutralization of the sterilizing chamber. To prevent the pressure in the sterilizing chamber and in particular also in the recovery cycle from dropping or at least from dropping too fast, at least a part of the separated sterilizing gas is replaced by addition of inert-rendering gas. By the addition of such a gas, which is preferably an inert gas and particularly preferably nitrogen, the sterilizing chamber is moreover advantageously flushed. Due to the metered addition of inert-rendering gas, in this connection reference only being made to nitrogen as a representative of such gases, the recovery apparatus is not unnecessarily loaded by excessive amounts of nitrogen. This is however the case when nitrogen is simply forced into the chamber for expelling the sterilizing gas. Moreover, compared with such a method there is a saving of nitrogen. Thus, one may dispense with complicated evacuating systems in the recovery cycle.

According to a preferred embodiment of the invention the metering of the added nitrogen is carried out in dependence upon the pressure in the sterilizing chamber. The sterilizing gas in the sterilizing chamber is particularly preferably replaced continuously, i.e. with diminishing addition rates of the nitrogen, until the concentration of the sterilizing gas in the chamber has dropped below a predetermined value. Expediently, this value lies at or beneath the value corresponding to a harmless residual gas concentration so that the sterilizing gas chamber can be opened again for charging with new materials for the next sterilizing cycle.

To enable the recovery cycle for the sterilizing gas to be operated particularly effectively, but also with a view to maximum safety regarding leakages which can never wholly be excluded, the method according to the invention runs at a substantially constant chamber pressure. Thus, the amount of additional nitrogen supplied to the sterilizing chamber is always approximately that necessary to compensate for the separated sterilizing gas in the sense of maintaining the pressure in the chamber. In an effectively iterative manner the separated sterilizing gas is continuously replaced by nitrogen. In a very particularly preferred manner, this chamber pressure to be maintained lies in the vicinity of the ambient pressure of the sterilizing chamber or the recovery apparatus, generally corresponding to atmospheric pressure. This largely eliminates the danger of an escape of sterilizing gas from the apparatus and entry of oxygen into the apparatus due to leakages, for example cracks.

The recovery cycle for the sterilizing gas includes a drying section and a low-temperature section. In the drying section the gas flow withdrawn from the sterilizing chamber is freed from moisture and in the low-temperature section part of the sterilizing gas contained in the dried gas flow is liquefied and separated. Between the drying section and the low-temperature section of the recovery cycle, according to a preferred embodiment of the invention, a heat exchanger is arranged which advantageously serves to effect a heat exchange between the gas flow, which has been heated due to the adsorption of moisture in an adsorber of the drying section, and the gas flow which is freed from the separated sterilizing gas and which is returned to the sterilizing chamber.

With the arrangement of such a recuperator, according to the invention, first the necessary refrigeration power of the low-temperature section for liquefying the sterilizing gas is reduced and second the residual gas to be returned to the sterilizing chamber is preheated.

Due to the low pressure differences in the method according to the invention, a fan for maintaining the recovery cycle suffices for the return of the residual gas to the sterilizing chamber.

The addition of the nitrogen replacing the separated sterilizing gas is carried out according to the invention via a controllable metering means, in particular a controllable metering valve. Said metering means is controlled by a controller in dependence upon one or more pressure sensors arranged in the sterilizing chamber. For this purpose, preferably a proportional integral (PI) controller is provided so that the control of the metering means is iteslf carried out with a certain regard to varying pressure conditions within the sterilizing chamber.

BRIEF DESCRIPTION OF THE DRAWINGS

A particularly preferred embodiment of the invention will be described hereinafter with the aid of the FIGURE. Further features and advantages of the invention will be apparent therefrom.

DESCRIPTION OF THE PREFERRED EMBODIMENT

The FIGURE illustrates the schematic construction of an apparatus for recovery of a sterilizing gas. After charging with the materials to be sterilized, a sterilizing chamber 1 is first evacuated by a vacuum pump 7 with the valve 2 open and the valves 3, 4, 5 and 6 closed. Thereafter, after closing of the valve 2 the sterilizing chamber is charged with a mixture of ethylene oxide (ETO) and nitrogen in the composition of about 40% ETO and 60% nitrogen.

It is pointed out that for the sterilization pure ETO may also be used, or a mixture of ETO and nitrogen, in particular with an ETO content of 10 to 60% and a corresponding nitrogen content of 40 to 90%. Fundamentally, to render the ETO inert other gases are also suitable. However, due to its easy handling and economy, as well as its environment compatibility, nitrogen is of prime importance here.

The filling of the sterilizing chamber 1 with sterilizing gas is initiated by opening the valves 4 and possibly 8 and subsequent opening of the valves 6 and 13. As a result, ETO passes from an ETO tank 9 under intrinsic pressure or from an ETO buffer 10, likewise under intrinsic pressure, via an ETO evaporator 11 into the sterilizing chamber 1, whilst nitrogen is conducted to the sterilizing chamber 1 from a tank 12 for liquid nitrogen via a nitrogen evaporator 14, conduits 35 and 40 and a controllable valve 16. After filling of the sterilizing chamber 1 with the ETO or the ETO/nitrogen mixture, the internal pressure of the sterilizing chamber 1 should correspond substantially to the ambient pressure. The valve 4 is now closed. The valve 16 is controlled by a controller 15 in dependence upon the pressure in the sterilizing chamber 1 via a control conduit 32 so that approximately ambient pressure always obtains in the sterilizing chamber 1.

After the ETO has acted upon the materials to be sterilized for a sufficient time, the sterilizing operation is terminated. To recover the ETO the valves 3 and 5 are opened and a fan 17 set in operation. This gives a closed circuit for recovering the sterilizing gas from the sterilizing chamber 1. A gas stream withdrawn from the sterilizing chamber 1 and containing the sterilizing gas is conducted consecutively through the following components: precooler 18-water separator 19-dryer 20-recuperator 21-low-temperature condenser 22-ETO separator 23-recuperator 21-fan 17 and conduits 30, 40 back into the sterilizing chamber 1. The gas flow conducted in this cycle is not connected in any manner to the environment. The gas flow from the sterilizing chamber 1 is cooled in the precooler 18 to a little more than 0° C. in particular to 4° to 10° C. The major part of the water vapour contained in the gas flow thereby condensed is separated in the following water separator 19. The gas flow is now supplied to a dryer 20, constructed in particular as adsorber, i.e. as molecular sieve 20. Almost the entire residual moisture is withdrawn from the already predried gas flow in the adsorber 20. The dew point of the gas flow leaving the adsorber 20 lies in the range between −80° and −100° C. In the cycle, ETO is continuously liquefied in the low-temperature condenser 22, the liquid phase separated by deposition in an ETO separator 23 and stored in liquid form in an ETO buffer 10. The ETO removed by the separation is replaced via the valve 16 controlled by the controller 15 by nitrogen which comes from the liquid nitrogen tank 12, so that the pressure in the sterilizing chamber 1 and thus in the entire recovery circuit is kept constant. This enables at least method-inherent pressure fluctuations to be avoided in the cycle. To enable a certain derivative reaction to varying pressures in the sterilizing chamber, the controller 15 is constructed as proportional-integral (PI) controller.

During operation of the fan 17 the ETO content in the cycle continuously diminishes with simultaneous increase in the nitrogen content. When the ETO content in the sterilizing chamber 1 has dropped to such an extent that it is below the limits allowed by the authorities, the valves 3, 5 and 6 are closed and the fan 17 switched off. The recovery is then completed and the sterilizing chamber 1 can be opened.

Apart from the nitrogen from the nitrogen tank 12 supplied to the sterilizing chamber 1, from the same tank 12 liquid nitrogen is withdrawn for cooling the low-temperature condenser 22. Via a valve 24 arranged downstream of the low-temperature condenser 22 this cooling power can be regulated.

A substantial part of the liquid nitrogen originating from the nitrogen tank 12 is used in a heat exchanger 41 for cooling an intermediate refrigerant circuit 42 with for example R 22 at about −85° to −90° C., which in turn through a heat exchanger 25 holds the ETO stored in the ETO buffer at for example about −80° C. The amount of liquid nitrogen necessary for this purpose can again be regulated by a valve 26.

Between the drying section of the recovery circuit formed by the precooler 18, the water separator 19 and the adsorber 20, and the low-temperature section including essentially the low-temperature condenser 22 and the ETO separator 23, the recuperator 21 is arranged. As a result, the gas stream, which is still warm, i.e. reheated in the adsorber 20 formed as molecular sieve, and the gas stream cooled in the low-temperature condenser 22 and freed from separated ETO in the ETO separator 23, are precooled and preheated in mutual heat exchange. This manner of heat recycling benefits the energy balance of the recovery because as a result the amount of nitrogen necessary for the cooling of the low-temperature condenser 22 can be kept small.

We claim:

1. A method for recovering a sterilizing gas such as ethylene oxide, comprising the steps of
    a) sterilizing materials in a sterilizing chamber with a sterilizing gas,
    b) extracting a gas containing said sterilizing gas from said sterilizing chamber to produce an extracted gas,
    c) liquefying a part of the sterilizing gas contained in said extracted gas to produce a liquefied sterilizing gas,
    d) separating said liquified sterilizing gas from a non-liquefied portion of said extracted gas, and
    e) returning said non-liquefied portion of said extracted gas to said sterilizing chamber, and continuously replacing at least a part of said liquefied sterilizing gas with an inert gas by supplying at diminishing addition rates said inert gas to said sterilizing chamber thereby reducing the concentration of said sterilizing gas in the sterilizing chamber.

2. A method according to claim 1, wherein the addition of said inert gas is metered to maintain a substantially constant pressure in said sterilizing chamber.

3. A method according to claim 1, wherein said sterilizing gas in said sterilizing chamber is replaced with said inert gas continuously with diminishing addition rates of said inert gas until the concentration of said sterilizing gas in said sterilizing chamber has dropped beneath a predetermined value.

4. A method according to claim 1, wherein said extracted gas extracted from said sterilizing chamber is cooled in a precooler which condenses a major part of water vapor entrained by said extracted gas, and conducted through a water separator which separates said condensed water vapor from said extracted gas.

5. A method according to claim 4, wherein residual moisture remaining in said extracted gas is removed in an adsorber comprising in particular a molecular sieve.

6. A method according to claim 1, wherein the non-liquefied portion of said extracted gas is heated by heat exchange with a gas flow from an adsorber before being returned to the sterilizing chamber.

7. A method according to claim 1, wherein the non-liquefied portion of said extracted gas is added to said inert gas before being returned to said sterilizing chamber.

8. A method according to claim 1, wherein said sterilizing gas comprises pure ethylene oxide.

9. A method according to claim 1, wherein said pressure in said sterilizing chamber corresponds substantially to the atmospheric pressure.

10. A method according to claim 1, wherein said sterilizing gas comprises 20–50% ethylene oxide and the remainder is an inert gas.

11. A method according to claim 10, wherein said inert gas is nitrogen.

12. A method according to claim 1, wherein said sterilizing gas comprises 40% ethylene oxide and the remainder is inert gas.

13. A method according to claim 12, wherein said inert gas is nitrogen.

* * * * *